United States Patent [19]

Norem et al.

[11] Patent Number: 5,013,528

[45] Date of Patent: * May 7, 1991

[54] ANALYSIS OF ORGANIC MATERIAL

[75] Inventors: Stanley D. Norem, Bayside, N.Y.; Richard T. Ferranti, Huntington; Robert F. Culmo, Woodbridge, both of Conn.

[73] Assignee: The Perkin-Elmer Corporation, Norwalk, Conn.

[ * ] Notice: The portion of the term of this patent subsequent to Jan. 3, 2006 has been disclaimed.

[21] Appl. No.: 218,721

[22] Filed: Jul. 13, 1988

Related U.S. Application Data

[62] Division of Ser. No. 19,905, Feb. 27, 1987.

[51] Int. Cl.$^5$ .............................................. G01N 31/21
[52] U.S. Cl. ..................... 422/94; 73/23.22; 73/23.35; 73/23.42; 422/83; 422/88; 422/89; 436/160; 436/161
[58] Field of Search .......... 422/83, 88, 89, 94; 436/160, 161; 73/23.22, 23.35, 23.42

[56] References Cited

U.S. PATENT DOCUMENTS

| | | | |
|---|---|---|---|
| 3,698,869 | 10/1972 | Condon | 436/160 |
| 4,650,499 | 3/1987 | Scott | 422/89 |
| 4,795,614 | 1/1989 | Norem et al. | 422/94 |

OTHER PUBLICATIONS

Rezl and Uhdeová, "Frontal Gas Chromatography as an Analytical Tool" in American Laboratory, Jan. 1976.

Lederer, E. and Lederer, M., *Chromatography*, Amsterdam, Elsevier Publishing Co., 1957, pp. 3–7.

*Primary Examiner*—Robert J. Warden
*Assistant Examiner*—Howard Hampel
*Attorney, Agent, or Firm*—H. S. Ingham; E. T. Grimes

[57] ABSTRACT

Apparatus is disclosed for quantitatively analyzing a gaseous mixture for its components. A predetermined volume of a gaseous mixture of combustion products component is collected in a gas mixer up to a preselected pressure. A portion of the mixture is discharged successively through the tubular column and a sample chamber for a predetermined time period with the mixture being initially at the preselected pressure in the volume means. Detection of delayed output of gas constituents from the column provides an analysis of constituents. The apparatus further comprises a furnace, a magazine for holding the plurality of test samples, a transfer device connected to the furnace for sequentially transferring a successive sample from the magazine to the furnace, and a furnace seal integral with the transfer device for temporal sealing of the furnace from ambient atmosphere after the sample is transferred to the furnace until subsequent transferral. A gas mixing system for homogenizing the gaseous mixture at a substantially constant temperature comprises a sealable vessel, an impeller rotatably mounted in the vessel for stirring the gases, wherein the impeller means comprises a plurality of blades each formed of a material having a mass such that the total heat capacity of the blades and the thermal conductivity of the blade material are cooperative with the impeller rotation to maintain constant temperature during introduction of the gases.

2 Claims, 4 Drawing Sheets

ANALYSIS OF ORGANIC MATERIAL

This is a continuation of co-pending application Ser. No. 019,905 filed on Feb. 27, 1987.

This invention relates to apparatus and method for quantitatively analyzing gaseous mixtures, particularly mixtures containing the gaseous combustion products of organic samples.

BACKGROUND OF THE INVENTION

Systems are used analyzing organic samples by way of combusting a sample and analyzing the gaseous products. For example, U.S. Pat. No. 3,252,759 (Simon) discloses a system in which gaseous combustion products are drawn into an enclosed reservoir that had been previously evacuated. The gas mixture is then released into a second evacuated vessel by way of a series of detectors that sequentially determine the amounts of such combustion product components as water and carbon dioxide in the mixture. Each detector comprises a pair of thermal conductivity measuring devices. The component being measured is removed from the gas mixture between the first and second devices in the pair, and the difference between the measurements, with calibration, provides the amount of the constituent.

U.S. Pat. No. 3,698,869 (Condon) avoids alleged problems of the Simon system, with its vacuum requirements, by operating above atmospheric pressure. The combustion products are mixed with and forced under the pressure of an inert carrier gas into a reservoir. A pressure switch in a gas line leading out of the reservoir shuts a valve between the combustion train and the reservoir. The gas mixture from the reservoir is then passed into a "delay volume" in the form of a coiled tube. Time periods are successively allowed in both the reservoir and the "delay volume" to complete mixing of the gases. The mixture in the "delay volume" is then shut off from the reservoir and forced from the "delay volume" through a series of detectors at constant pressure by the carrier gas source and vented to atmosphere. The detectors are of the type disclosed in Simon and vented to atmosphere. Although the Condon system has proven to be quite practical and successful, there is still a substantial need for increased speed of operation, accuracy and simplification of operation.

A modified technique is taught in "Frontal Gas Chromatography as an Analytical Tool" by Vlastimil Rezl and Jitka Uhdeova, *American Laboratory*, January 1976, Pages 13-26. A chromatographic column formed of a coiled tube containing gas adsorption material is substituted for the "delay volume" tube, and a single detector receives the flow output from the column. Gas components are successively adsorbed. The heights of the adsorption steps of the components displayed from the detector signal are used (again with calibration) to provide the quantitative analysis. Rezl et al. describe the technique in a system that involves constant pressure flow through the column, achieved with a dilution chamber containing an easily movable piston maintained under constant gas pressure from the back side. The Rezl system involves a substantial degree of complexity of gas lines and valving.

Related concerns to improve operating efficiency exist with respect to introducing samples of solid material into a system for analysis. It is desirable to have an apparatus for loading the samples into the furnace with a minimum of time and dead volume of gas, and with a simple, efficient system for sealing from the ambient atmosphere.

U.S. Pat. No. 4,055,259 (Sibrava) discloses a sample transport apparatus for conveying test samples horizontally from a source into a combustion chamber. Samples are initially contained in a motor driven rotary magazine. A sample is dropped from the magazine into an aperture in a motor-driven rotary transfer plate. The plate is rotated a half turn to drop the sample through a passage onto a sample transport member. The sample transport member rides horizontally into a conduit which extends to the furnace. The sample transport member is conveyed to the furnace by means of a motor-driven tape. A reversed procedure is used to withdraw and drop the solid remnants of combustion through a second rotary plate and a second passage out of the apparatus. Sealing of the various orifices is accomplished by means of O-rings on which the sample plates ride.

Sample introduction into a vertically aligned furnace is disclosed in U.S. Pat. No. 4,525,328 (Bredeweg). A set of jaws is displaced horizontally to grab a sample, which is then moved over to the top of the furnace inlet and released by the jaws.

The above-described transport devices are workable in varying degrees but suffer from the complexity of motors or interconnecting gears (or pulleys) and from the unreliability of sliding seals.

Therefore, an object of the present invention is to provide an improved apparatus and method for analysis of gaseous mixtures.

Another object is to provide novel gas analysis apparatus having improved speed of operation, accuracy and simplification of operation.

Yet another object is to provide an improved system for analysis of organic samples by analyzing gaseous combustion products.

A further object is a novel system for rapid transfer of samples into a testing apparatus with reliable sealing against ambient atmosphere.

SUMMARY OF THE INVENTION

The foregoing and other objects of the present invention are achieved by apparatus for quantitatively analyzing a gaseous mixture for its components comprising volume means for collecting a predetermined volume of a gaseous mixture of a base component and at least one additional component, pressurized fluid means connected to force the gaseous mixture into the volume means up to a preselected pressure, a tubular column having an input end and an output end, the input end being in fluid flow relationship with the reservoir means, sample chamber means in fluid flow relationship with the output end of the tubular column, discharge means for discharging a portion of the mixture from the volume means successively through the tubular column and the sample chamber means for a predetermined time period with the mixture being initially at the preselected pressure in the volume means, extracting means in the tubular column for extracting a predetermined amount of the additional component from the mixture during the predetermined time period, and component detection means communicating with the sample chamber for detecting the amount of the additional component in the gaseous mixture in the sample chamber during the predetermined time period.

The apparatus further comprises combusting means for sequentially combusting each of a plurality of test samples to produce as combustion product at least one component of the gaseous mixture, the combusting means including a furnace, a magazine for holding the plurality of test samples, transfer means connected to the furnace for sequentially transferring a successive sample from the magazine to the furnace, furnace sealing means integral with the transfer means for temporal sealing of the furnace from ambient atmosphere after the sample is transferred to the furnace until subsequent transferal, and means for introducing oxygen into the furnace. The transfer means comprises a body with a drop section, a piston end, a body chamber therein extending horizontally from the drop section to the piston end, a body aperture extending from the body chamber upwardly through the body so as to be receptive of the sample, and a drop port in the drop section extending downwardly through the body from a point in the body chamber vertically offset from the body aperture. A piston member is slidingly situated in the body chamber such as to have a first position and a second position. Guide means for guiding the sample coact with the piston member so as to be receptive of the sample from the body aperture when the piston member is at the first position and vertically aligned with the drop port when the piston is at the second position. Retaining means temporarily retain the sample in the guide means. Releasing means release the sample from the guide means through the drop port.

The apparatus further comprises a gas mixing system for homogenizing the predetermined volume of the gaseous mixture at a substantially constant temperature, comprising a sealable vessel having a net volume, gas means for introducing the plurality of gases into the vessel at increasing pressure in the vessel up to a predetermined pressure, impeller means rotatably mounted in the vessel for stirring the gases, and rotating means for rotating the impeller at a high speed, wherein the impeller means comprises a plurality of blades each formed of a material having a mass such that the total heat capacity of the blades and the thermal conductivity of the blade material are cooperative with the impeller rotation to maintain the temperature within 1° C. during introduction of the gases at a rate of 1 atmosphere in 10 seconds while the gases are being stirred at the high speed.

BRIEF DESCRIPTION OF THE DRAWINGS

FIG. 8 is a side view in vertical section of a unitary fluid flow manifold according to the present invention.

FIGS. 9a and 9b are schematic diagrams of respective settings of a gas switching system utilized in the apparatus of FIG. 1.

DETAILED DESCRIPTION OF THE INVENTION

Figure 1:
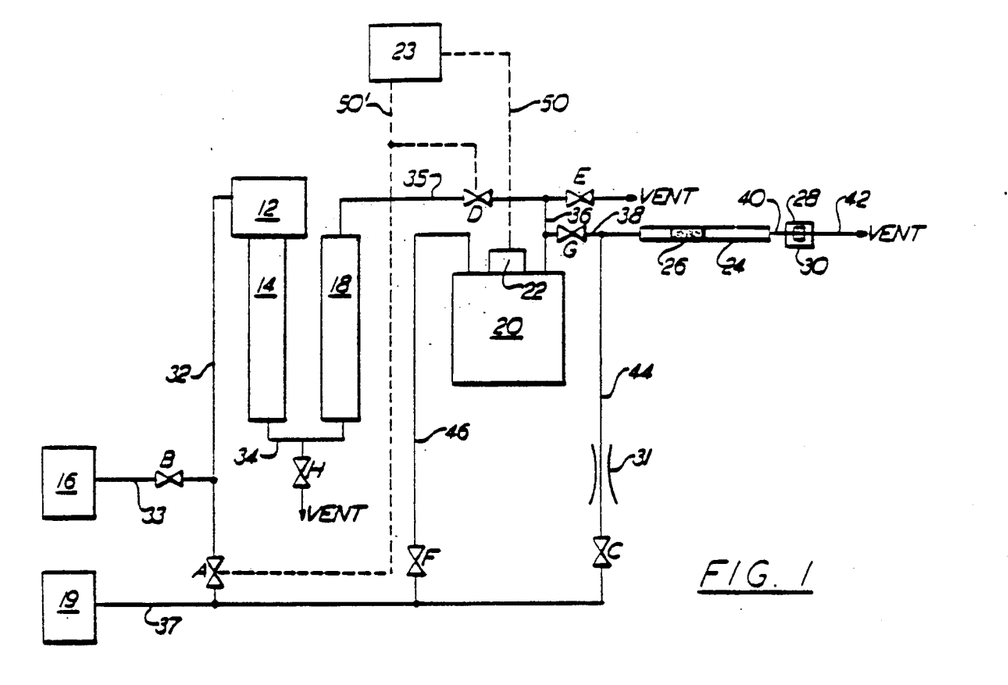
FIG. 1 is a schematic diagram of an apparatus according to the present invention.

FIG. 1 shows a block diagram of an apparatus for combusting a sample and quantitatively analyzing the gaseous mixture of combustion products for its components, according to the present invention. For accuracy and speed critical portions of the system are contained in an insulated oven (not shown) maintained at 82° C. The apparatus includes a sample loader 12 located above a combustion furnace 14 for loading a test sample into the furnace. The sample may be in the form of a pellet, a sample enclosed in tin foil or the like or other convenient form. For typical organic samples the furnace is maintained at about 950° C.

Oxygen is introduced into furnace 14 under pressure from an oxygen source 16 through a line 33, an opened valve B and a gas line 32. Ignition occurs at the furnace temperature. Combustion products are passed over catalytic agents in the lower portion of the furnace and thence through a line 34 to a reduction oven 18 at 650° C. containing copper to reduce oxides of nitrogen and remove all excess oxygen. At this stage the combustion products typically consist of water, carbon dioxide and nitrogen.

With oxygen valve B closed, the gaseous combustion products are then partially mixed with and forced under the pressure of an inert carrier gas such as helium or argon, from a source 19 via line 37 and opened valve A and line 32, through line 35, valve D and line 36 into an enclosed sample vessel 20. Thorough mixing is effected and a preselected pressure of about one atmosphere above ambient is reached in the vessel.

A pressure transducer 22 on sample vessel 20 detects when the preselected pressure is reached and generates an electrical signal which, through a controller 23 and electrical lines 50, 50' (shown dashed to distinguish from gas lines) closes carrier valve A and inlet valve D. After a short interval of further mixing of the carrier gas and the combustion products in the vessel, valve G is opened and the mixture is forced by its elevated pressure into and through a tubular column 24 via a line 38. Although shown foreshortened in FIG. 1 for clarity, the tubular column is conveniently a coiled length of tubing. Adsorbent material 26 in the column selectively absorbs and determines the rate of passage of the individual combustion products in the gas mixture.

The time variant gas composition then passes through a line 40 and into a sample chamber 28 containing a detector 30 that measures a physical property of the gas mixture that depends on its composition. Preferably the detector is a thermistor, measuring thermal conductivity. The mixture is subsequently vented through a line 42 to atmosphere.

Figures 2, 3:
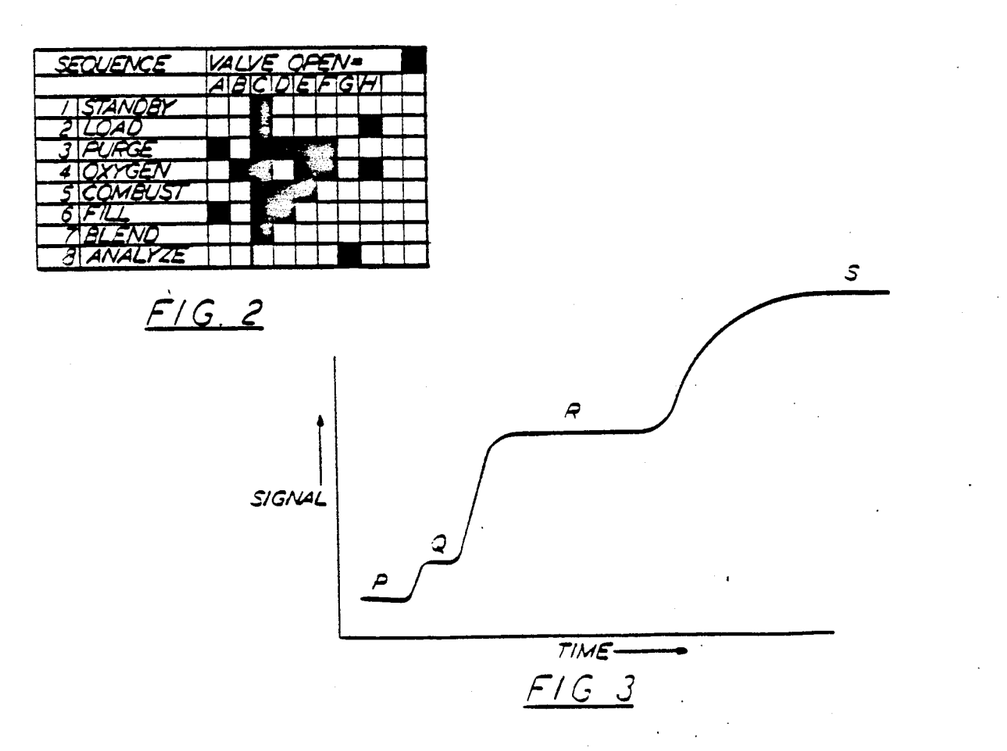
FIG. 2 is a graphic presentation of sequencing of the valving depicted in FIG. 1.
FIG. 3 is a graph of signal output from a detector depicted in FIG. 1.

FIG. 2 shows the sequence of steps and the associated valve positions of the valves indicated in FIG. 1. During standby valve C feeding the inert carrier gas through a constrictor 31 and a gas line 44 is open and the helium is used to purge column 24 and sample vessel 20. Optionally valves D, E and F are also open for purging and the next step. This purging is maintained during all subsequent steps except analysis as described below. While the sample is loaded into sample loader 12 valve H is opened to vent the furnace 14 and oven 18. After loading, various valves are set for purging the entire system with helium, as indicated in FIG. 2 with continuing reference to FIG. 1. For example, vessel 20 receives helium from valve F via a line 46 and is vented via line 36 and valve E. Oxygen is then introduced into furnace 14 with valve B and vent valve H both open, while valves A and D are closed and the helium continues purging the rest of the system.

For combustion the sample is dropped into the furnace where it is retained in a porous cup (not shown) of the type shown in aforementioned U.S. Pat. No. 4,525,328, oxygen valve B is shut off while venting furnace 14 and oven 18 through opened valves D and E, and purging of column 24 and sample chamber 28 continues through valve C. Combustion products are moved to sample vessel 20 with the carrier gas as valve A is opened and vent valve E closed. For the final step (analysis), all valves are closed except connecting valve G from vessel 20 to column 24. Purging is thus stopped and the pressure of the gases in vessel 20 forces the gases through column 24 and sample chamber 28 at a highly reproducible rate during the analysis phase.

FIG. 3 shows the type of signal output to be expected from the detector during the time period of the analysis step. Initially at phase "P" the signal reflects the property of the pure carrier gas. "Q" represents the mixture of the most mobile component (e.g. nitrogen) and carrier. "R" represents this mixture plus the next most mobile component (e.g. $CO_2$). "S" represents the mixture of all the components which can traverse the column (e.g. carrier plus $N_2$, $CO_2$ and $H_2O$).

The relative heights of the steps, with calibration, provide the guantitation analysis.

Column 24 is formed as a coiled length of tubing of stainless steel. It should be between 10 and 100 cm in length, preferably between 30 and 90 cm, for example 60 cm. The inside diameter is between 1 and 4 mm, preferably 1.5 and 2.5 mm, for example 2 mm. The adsorbent material 26 in the column is, for example, a porous polymer such as 80/100 mesh "Porapak" sold by Waters Associates.

It is important that the total system volume for the mixture be minimized, to gain rapidity in making the analyses and maximize accuracy of the measurements. Thus, according to the present invention, the single tubular column 24 containing adsorbent 26 replaces a number of components used heretofore, namely a sample volume and two separate sample traps and multiple detector cells for removing and detecting individual gas components in sequence. Accuracy and speed are also obtained by the fact that baseline measurements are made during the analysis stage, replacing a separate two-minute baseline run that was necessary in the past. Advantages include the economy and gas circuit simplification afforded by a single detector cell over the multiple cell configuration of Condon and complexities of Rezl. The column is "regenerated" by purging with carrier gas whereas absorbing traps must be refilled periodically. Further improvements in speed and accuracy are effected through the use of certain other components according to the present invention, as described below.

Figures 4, 4A:
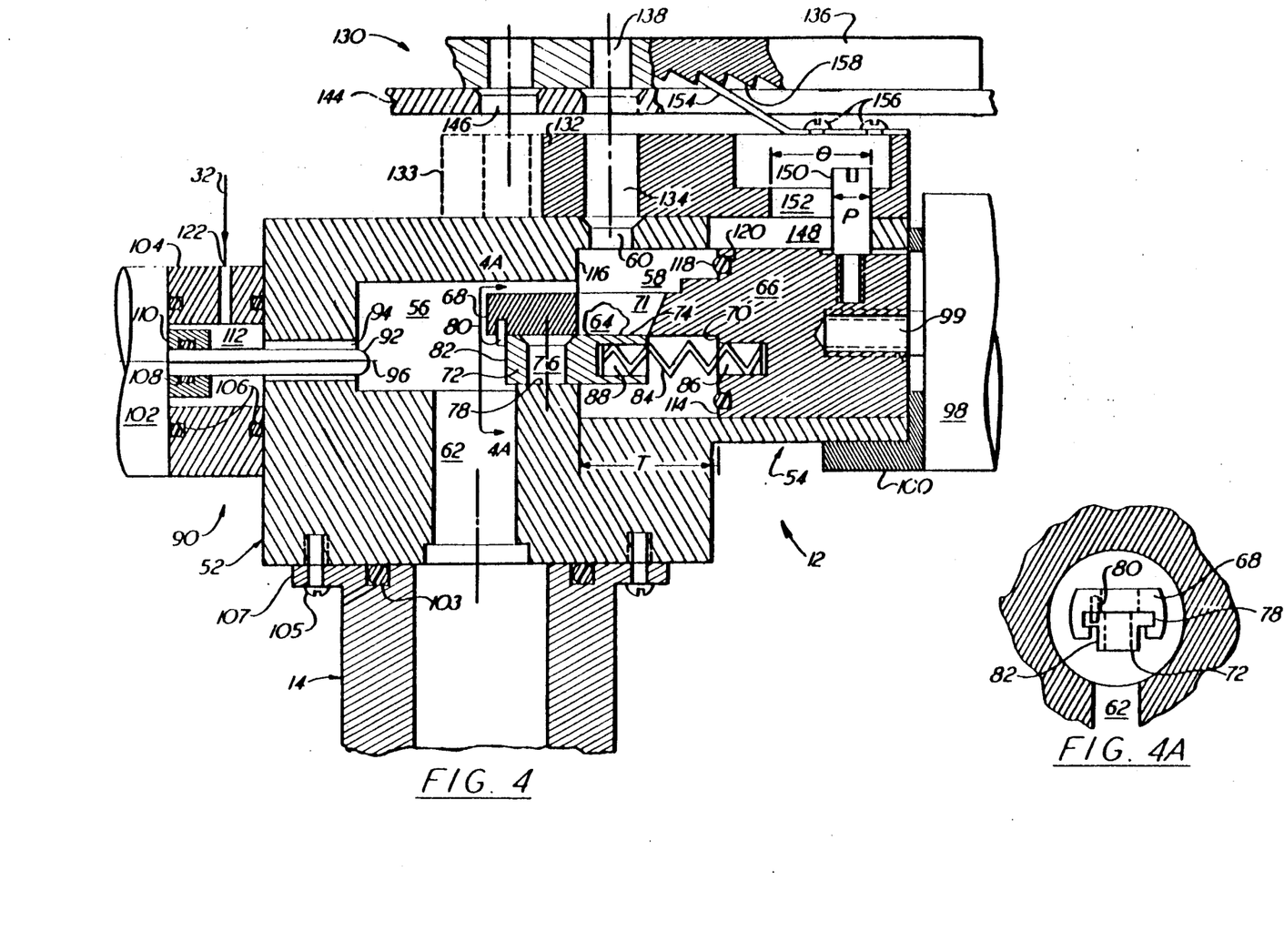
FIG. 4 is a side view in vertical section of a sample loading device according to the present invention.

A rapidly operating sample loading device 12 that adds a minimum of volume to the system is shown in FIG. 4. An elongated body 52 has a piston end 54, a body chamber generally comprising a central chamber 56 and a cylindrical cavity 58 extending generally horizontally from chamber 56 to piston end 54, a body aperture 60 extending from cylindrical cavity 58 proximate chamber 56 upwardly through the body, and a drop port 62 extending from chamber 56 downwardly through the body. Body aperture 60 is receptive of a sample 64 from above which is passed downwardly through port 134 in block 132.

A piston member 66 is slidingly situated in cylindrical cavity 58 such as to have an inner position adjacent to chamber 56 and an outer position away from the chamber; FIG. 4 shows the piston at the outer position. A guide member 68 is attached to the inner end 70 of piston 66 such a to protrude into chamber 56. Guide member 68 has a vertical guide aperture 71 therethrough that is alternatively aligned vertically with body aperture 60 (as shown) to receive sample 64 when piston 66 is at the outer position, or with drop port 62 when the piston is at the inner position.

A horizontally sliding sample-retaining door 72 is situated adjacently below guide member 68 and has a wall portion 74 for retaining sample 64, and a door aperture 76 adjacent to the wall portion extending vertically through the retaining door. As shown in FIG. 4A, the retaining door has a "T" shaped cross section and is slidingly supported in a track 78 in the underside of guide member 68. Wall portion 74 (FIG. 4) is located between door aperture 76 and piston 66. Retaining door 72 is positioned alternatively in a sample retaining position (shown in FIG. 4) or a sample drop position (not shown), each such position being with respect to guide member 68 such that wall portion 74 is aligned vertically with guide aperture 71 for the retaining position, and door aperture 76 is aligned vertically with guide aperture 71 for the drop position.

A compressed spring 84 is positioned from a first hole 86 in piston 66 to a second hole 88 in door 72. Spring 84 presses mating surface 82 against a positioning pin 80 in a direction away from piston 66 such that retaining door 72 is normally maintained in the retaining position shown in FIG. 4 by the spring.

A door actuator 90 is used for sliding retaining door 72 to the drop position while piston 66 is at its forward position, thereby releasing sample 64 through door aperture 76 and thence through drop port 62. A retractable actuator rod 92 extends loosely through a bore 94 in body 52 extending from chamber 56 in a direction generally parallel to and away from cylindrical cavity 58, rod 92 having an extended axis 96 which intersects retaining door 72. Thus rod 92 can be pushed against retaining door 72 to retract the door against spring 84 to the drop position and align door aperture 76 between guide aperture 71 and drop port 62, thus dropping sample 64 out of the loading device.

Piston 66 and actuator rod 92 may each be moved by hand or a solenoid, motor or the like, but pneumatic linear actuators of the known or desired type are desirable for each of these functions. In the present embodiment, a piston actuator 98 is mounted to body 52 with a spacer bracket 100, and a rod actuator 102 is mounted to the body with a mounting collar 104. (Mounting screws are not shown.)

Sample-receiving furnace 14 is sealed with an O-ring 103 under body 52 below the drop port, affording a minimum of internal volume, by screws 105 through a flange 107 on the furnace.

Mounting collar 104 is coaxial with bore 94 and is sealed between body 52 and actuator 102 with O-ring seals 106. An O-ring 108 seals an actuator flange 110 against rod 92 and allows the rod to slide therein, thus effectively providing sealing between the movable rod and the body. An annular cavity 112 is formed between collar 104 and rod 92.

Means is provided for sealing the chamber with the piston when the piston is at its forward position. Inner end 70 of piston 66 has a peripheral annular surface 114 perpendicular to the common axis of the piston and cylindrical cavity 58. The cylindrical cavity is bounded at the chamber by a second annular surface 116 that is parallel to and facing first surface 114 in alignment therewith. An O-ring seal 118 in an annular groove 120 in annular surface 114 (or in the second annular surface) effects a seal between chamber 56 and cavity 58 when piston 66 is at the forward position.

A gas inlet orifice 122 is provided for introducing oxygen and, as required, helium (or argon) into the chamber, via gas line 32 (FIG. 1), annular cavity 112 and bore 94, when piston 66 is at the inner position a which time chamber 56 is fully sealed from the ambient atmosphere except for the drop port 62 entrance to furnace 14.

A magazine loader 130 is mounted above body 52 for loading successive samples into body aperture 60. The magazine loader shown in top view in FIG. 5, as well as in FIG. 4, comprises a loading member 132 slidingly mounted on top of the body. The loading member has vertical loading aperture 134 therethrough that is receptive of the next sample from above when loading member 132 is in a forward position (indicated by dashed line 133). When member 132 is in the normal position loading aperture 134 is alignable with body aperture 60 to drop the next sample therethrough.

Figure 6:
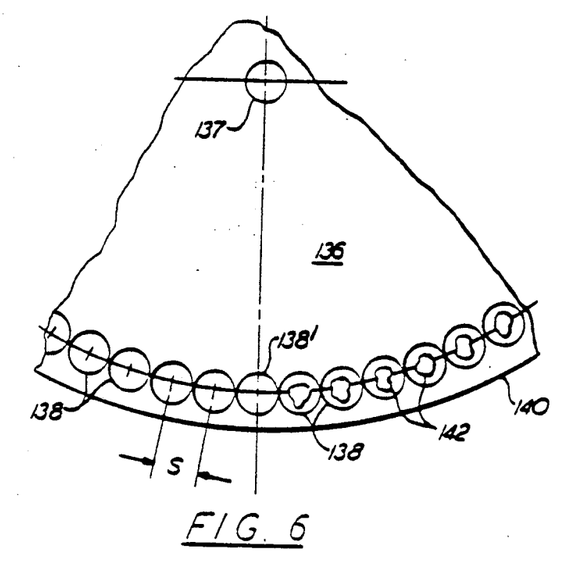
FIG. 6 is a top view of a magazine utilized with the device of FIG. 4.

A disk shaped magazine 136, a portion of which is also depicted in top view in FIG. 6, is mounted on an axle 137 and is positioned above loading member 132. The magazine has a plurality of equally spaced vertical magazine cavities 138 therethrough, the cavities being positioned arcuately near the rim 140 of the magazine disk. Each cavity (that has not yet supplied a sample) holds at least one of a plurality of samples 142. The magazine has successive loading positions and is movable to each of the successive loading positions.

Continuing with reference to FIG. 4, a ring-shaped mounting plate 144, of outer diameter comparable to that of magazine 136 is fixed with respect to body 52 and is juxtaposed closely between sample magazine 136 and loading member 132 to retain the plurality of samples 142 in the respective magazine cavities 138. (Mountings for the plate and magazine, not shown, are of conventional design.) A plate opening 146 extends vertically through mounting plate 144 and is located with respect to the magazine to pass a sample through from an adjacent magazine cavity 138', the magazine being in a loading position. Plate opening 146 is oriented vertically above aperture 134 when loading member 132 is in its forward position 133. When member 132 is retracted, a sample received through opening 146 is dropped through aperture 60.

Figure 5:
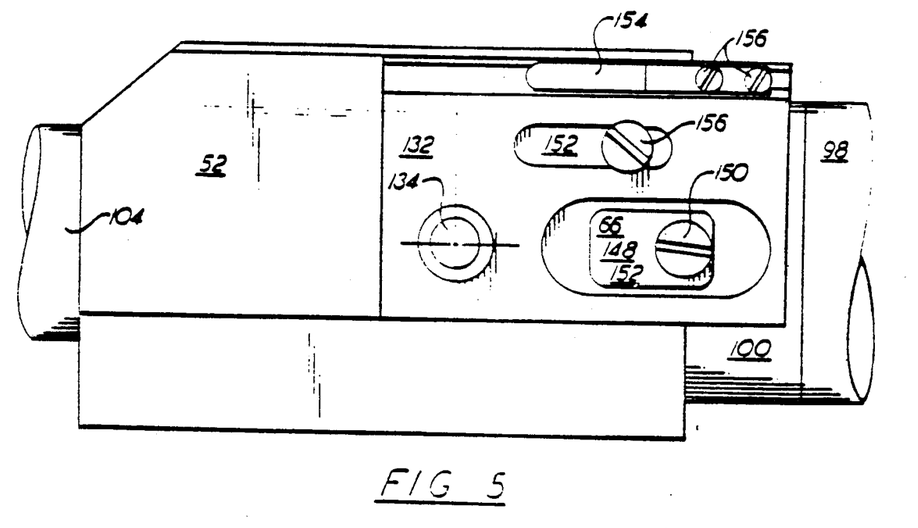
FIG. 5 is a top view of the device of FIG. 4.

Body 52 has an elongated pin opening 148 extending upwardly therethrough from cylindrical cavity 58. A pin 150 is threaded into piston 66 and extends radially upwards through pin opening 148. Loading member 132 on top of body 52 has a pin orifice 152 therein that allows member 132 to be engaged by pin 150. FIG. 5 shows a top view of the loading device without magazine or plate. A slot 154 in member 132 cooperates with a retaining screw 156 threaded into the top of body 52 to guide the loading member.

Continuing with FIG. 4, a drive pawl 154 is attached to the top of the loading member 132 with screws 156 (also in FIG. 5) Ratchet teeth 158 are equally positioned arcuately under magazine 136 near rim 140 (FIG. 6) but radially in from plate 144, in actuating contact with the drive pawl. Upon actuation of piston 66 from the outer position to the inner position pin 150, after a free motion, slides the loading plate such that drive pawl 154 moves magazine 136 to a subsequent loading position to deposit a new sample through plate opening 146 and aperture 134 to rest on top of block 52. When piston 66 is returned to its outer position pin 150 moves loading member 132 back so the sample is dropped through loading aperture 134 and body aperture 60. Thus the new sample is being loaded into the device while the previous sample 64 is being dropped into furnace 14.

To accommodate many samples the magazine has a separation distance "S" between each successive magazine cavity 138 and also between each ratchet tooth 158 (or a multiple number thereof) that is less than the travel distance "T" of piston 66 between the outer position and the inner position. Pin 150 has a diameter "P". Pin orifice 152 is a slot with a dimension "O" in the direction parallel to cylindrical cavity 58 such that $S+O=T+P$. Upon actuation of the piston from the outer position to the inner position, the pin has some free motion in the pin opening so as to slide the loading plate a distance only equal to the separation distance "S". For example, the pin is 9.5 mm in diameter, the elongated dimension of the pin opening in the loading plate is 22 mm, the travel distance of the piston is 25 mm, and the separation between cavities in the magazine is 11 mm and between ratchet teeth is 8 mm.

Figure 7:
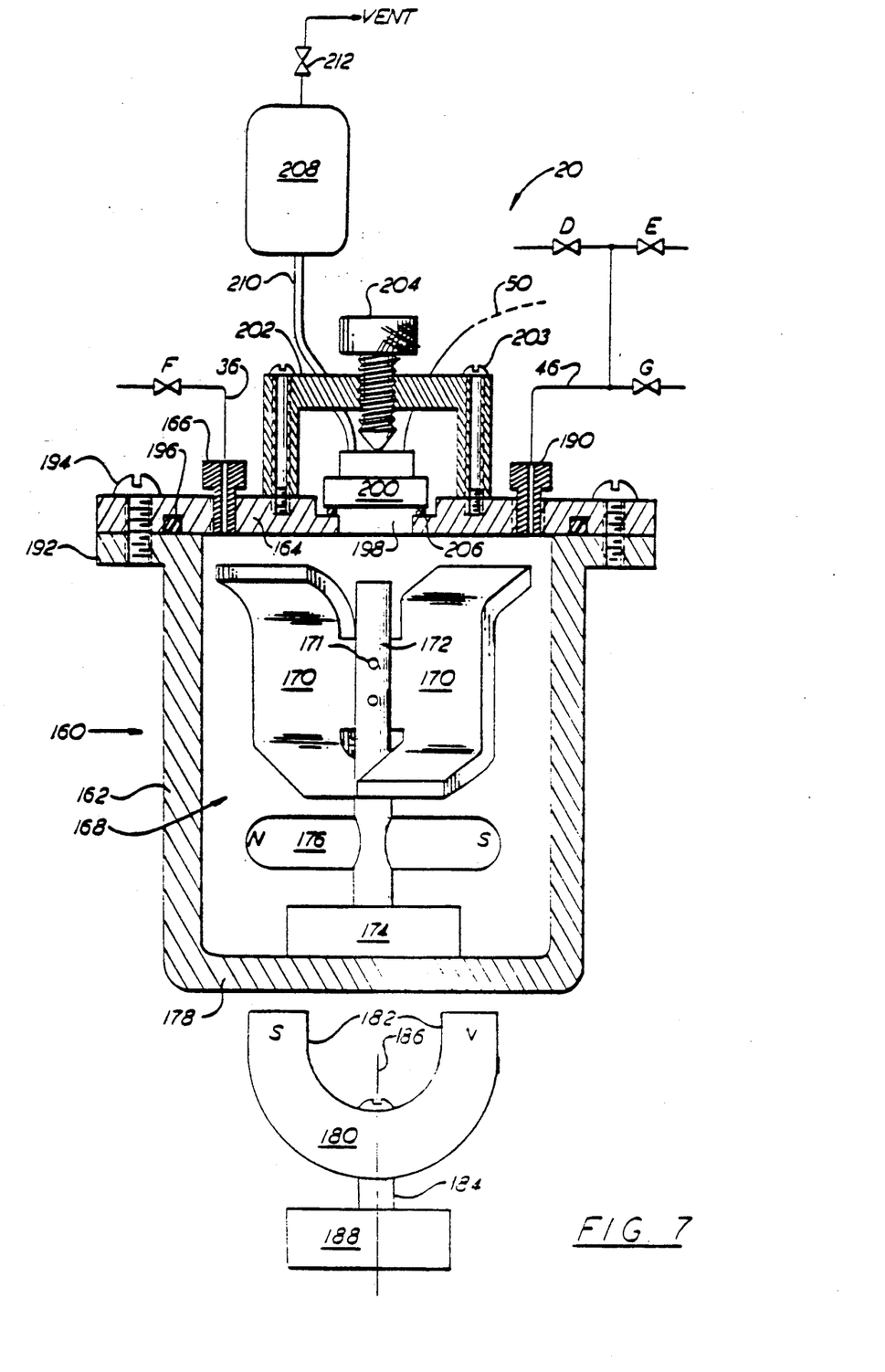
FIG. 7 is a side view in vertical section of a gas mixing vessel according to the present invention.

In a further embodiment of the present invention a unique gas mixing vessel 20, shown in FIG. 7, is used for homogenizing the gases at a substantially constant temperature while the gases are being introduced into the vessel at increasing pressure. In this embodiment a sealable vessel 160 is constructed of a casing 162 which includes a cover 164. A gas connection 166 receives the gaseous combustion products from line 36 under the pressure of the carrier gas. While the pressure in vessel 160 is increasing up to a predetermined pressure, and for a short time thereafter, an impeller 168 mounted in the vessel stirs the gases. The impeller desirably has two (or more) blades 170 mounted with pins 171 on a shaft 172 that rotates in a ball bearing assembly 174. Each blade preferably has a twisted "S" shape such as to impart an axial component to gas motion in the vessel to efficiently and rapidly mix the gases.

According to the present invention each blade 170 is formed of a material with a relatively high mass with a corresponding heat capacity and a thermal conductivity that are sufficiently high to effectively maintain constant temperature of the gas mixture in vessel 160 during pressurization. The purpose is to counter the tendency for the gases to increase in temperature during the inlet pressurization process. It is desirable to pressurize at a rate 1 atmosphere within 10 seconds, and it is highly desirable to maintain the temperature within 0.5° C. during gas input so that the volume of gas can be sent to the column as soon as mixing is completed, without waiting for the temperature to settle. Thus the cycling time for the analyses is further shortened.

The total heat capacity (i.e. specific heat times total mass) of the blades should be at least 30 times the total heat capacity of the gases in the vessel at the predetermined pressure. Thermal conductivity of the blade material should be at least 0.5 calories/sec ° C. cm relative to 1.0 for pure copper. Copper is preferable, gold plated to minimize contamination. For example for a mixing vessel having a net volume (with impeller and associated components in place) of 300 cc, copper blades with a total mass of 35 gm is desirable.

Continuing with FIG. 7, a PTFE plastic coated bar magnet 176 is mounted perpendicularly on shaft 172 inside vessel 160 proximate the lower end wall 178 of casing 162. A horseshoe magnet 180 with poles 182 aiming upwards is set on a vertical shaft 184 aligned with the impeller axis 186 and is located below the vessel proximate end wall 178. A motor 188 drives shaft 184, and the outside magnet 180 is magnetically coupled to the inside magnet 170 for rotating same and thereby rotating blades 170 at high speed, probably between 1000 and 3000, e.g. about 1500 rpm.

The gas connection components include valve D (and, as appropriate, valves E and G shown in FIG. 1) and tube section 36 connected between the valve and the vessel and, similarly, valve F and tube section 46 for a second gas connection 190. It is important that the tube sections 36,46 contribute only a very small volume to assure thorough mixing of the enclosed gases, e.g., less than 0.25% of the volume of vessel 160 containing impeller 168, for example having a length of 30 cm each and an inside diameter of 1 mm.

The top of the vessel casing comprises cover 164 held to a flange 192 with screws 194 and sealed against the flange with an O-ring seal 196. The cover includes the gas tube connections 166,190. An opening 198 in cover 164 provides for a differential pressure transducer 200 held over the opening with a yoke 202. The transducer may be of the conventional type, such as Model P612 sold by Kavlico Corp., Chatsworth, Calif. The yoke is attached to the cover with screws 203, and a thumb screw 204 presses the transducer against an elastomer face seal 206 on the cover. A buffer container 208 nominally at atmospheric pressure is connected via a tube 210 to the transducer to provide a control pressure unperturbed by short term fluctuations in ambient pressure. A vent valve 212 allows resetting the buffer pressure. The close proximity of transducer 200 to opening 198 in the vessel casing further minimizes extraneous volume for the mixing process.

Transducer 200 is set to detect when the pressure from the input gases reaches a predetermined pressure, for example about one atmosphere above ambient and generally in the range of about half to 1.3 atmospheres. Referring also to FIG. 1, electrical signals through lines 50,50' and controller 23 closes carrier gas inlet valves A and D when the vessel pressure reaches the predetermined pressure.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

What is claimed is:

1. Apparatus for quantitatively analyzing a gaseous mixture for its components, comprising:
    a fixed-volume vessel for collecting a gaseous mixture;
    pressurized fluid means connected to force a gaseous mixture of a base component and a plurality of additional components into the vessel up to a preselected pressure;
    a chromatographic column having an input end and an output end, the input end being in fluid flow relationship with the vessel;
    a sample chamber in fluid flow relationship with the output end of the tubular column;
    discharge means for discharging a portion of the mixture from the vessel successively through the column and the sample chamber for a predetermined time period with the mixture being initially at the preselected pressure in the vessel;
    extracting means disposed in the column for extracting a predetermined amount of each additional component from the mixture such as to produce a time variant composition of the mixture in the sample chamber during the predetermined time period; and
    component detection means consisting of a single detector communicating with the sample chamber for detecting a physical property of the mixture dependent on the time variant composition such as to provide a measure of the amount of each of the additional components in the gaseous mixture in the sample chamber during the predetermined time period.

2. Apparatus for quantitatively analyzing a gaseous mixture for its components, comprising:
    a fixed-volume vessel for collecting a gaseous mixture;
    pressurized fluid means connected to force a gaseous mixture including a base component, a first additional component and a second additional component into the vessel up to a preselected pressure;
    valve means for isolating the vessel from the pressurized fluid means after the gaseous mixture in the vessel is at the preselected pressure;
    a chromatographic column having an input and an output end, the input end being receptive of gas flow from the vessel;
    a sample chamber receptive of gas flow from the output end of the column;
    discharge means for discharging a gas flow consisting of an undiluted portion of the gaseous mixture from the vessel successively through the column and the sample chamber for a predetermined time period with the mixture being initially at the preselected pressure;
    extracting means disposed in the column for extracting predetermined amounts of the first and second additional components from the mixture such as to produce a time variant composition of the mixture in the sample chamber, the predetermined time period being sufficiently long for the time variant composition to be formed of, successively, the base component, a first mixture of the base component and the first component, and a second mixture of the first mixture and the
    detector means consisting of a single detector communicating with the sample chamber for detecting a physical property of the mixture dependent on the time variant composition such as to provide a measure of the amount of each of the additional components in the mixture in the sample chamber.

* * * * *

UNITED STATES PATENT AND TRADEMARK OFFICE
CERTIFICATE OF CORRECTION

PATENT NO. : 5,013,528
DATED : May 7, 1991
INVENTOR(S) : Stanley D. norem, Richard T. Ferranti and Robert F. Culmo It is certified that error appears in the above-indentified patent and that said Letters Patent is hereby corrected as shown below:

In column 10, line 58, after "and the" insert --second component; --.

Signed and Sealed this

Thirteenth Day of July, 1993

Attest:

MICHAEL K. KIRK

Attesting Officer     Acting Commissioner of Patents and Trademarks